(12) United States Patent  (10) Patent No.: US 7,641,655 B2
Shores et al.  (45) Date of Patent: Jan. 5, 2010

(54) COUPLING SYSTEM FOR SURGICAL INSTRUMENT

(75) Inventors: Rex Wesley Shores, Norfolk, MA (US); Paul A. Cihak, Grapevine, TX (US); Larry D. Estes, North Richland Hills, TX (US)

(73) Assignee: Medtronic, Inc., Minneapolis, MN (US)

( * ) Notice: Subject to any disclaimer, the term of this patent is extended or adjusted under 35 U.S.C. 154(b) by 495 days.

(21) Appl. No.: 10/698,638

(22) Filed: Oct. 31, 2003

(65) Prior Publication Data

US 2005/0096662 A1  May 5, 2005

(51) Int. Cl.
*A61B 17/00* (2006.01)
(52) U.S. Cl. .................................................. 606/79
(58) Field of Classification Search ............ 606/79, 606/80; 279/75
See application file for complete search history.

(56) References Cited

U.S. PATENT DOCUMENTS

| | | | | |
|---|---|---|---|---|
| 4,060,219 A | * | 11/1977 | Crawford | 251/149.6 |
| 5,123,446 A | * | 6/1992 | Haunhorst et al. | 137/614.02 |
| 6,062,575 A | * | 5/2000 | Mickel et al. | 279/75 |
| 6,116,902 A | * | 9/2000 | Schodel et al. | 433/89 |

* cited by examiner

*Primary Examiner*—Eduardo C Robert
*Assistant Examiner*—Elana B Fisher
(74) *Attorney, Agent, or Firm*—Haynes and Boone LLP

(57) ABSTRACT

The present invention provides improved coupling arrangements for medical instruments. In one example, a coupling system for a medical dissection tool includes: an internal passage adapted for receiving a portion of a medical dissection tool; and at least one locking member movable through a first angled path into a locked position to prevent the medical dissection tool from moving along a longitudinal axis of the internal passage.

10 Claims, 4 Drawing Sheets

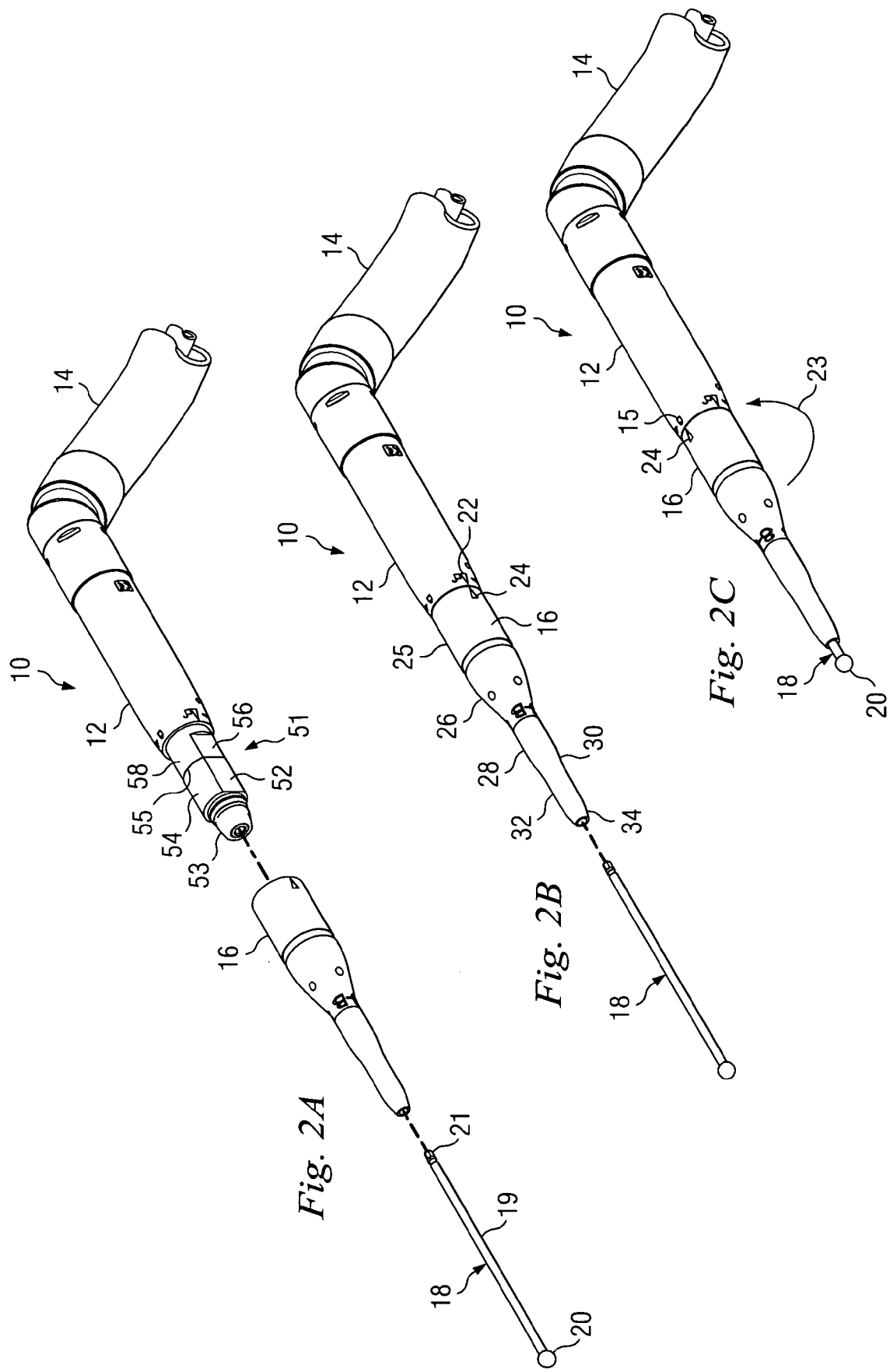

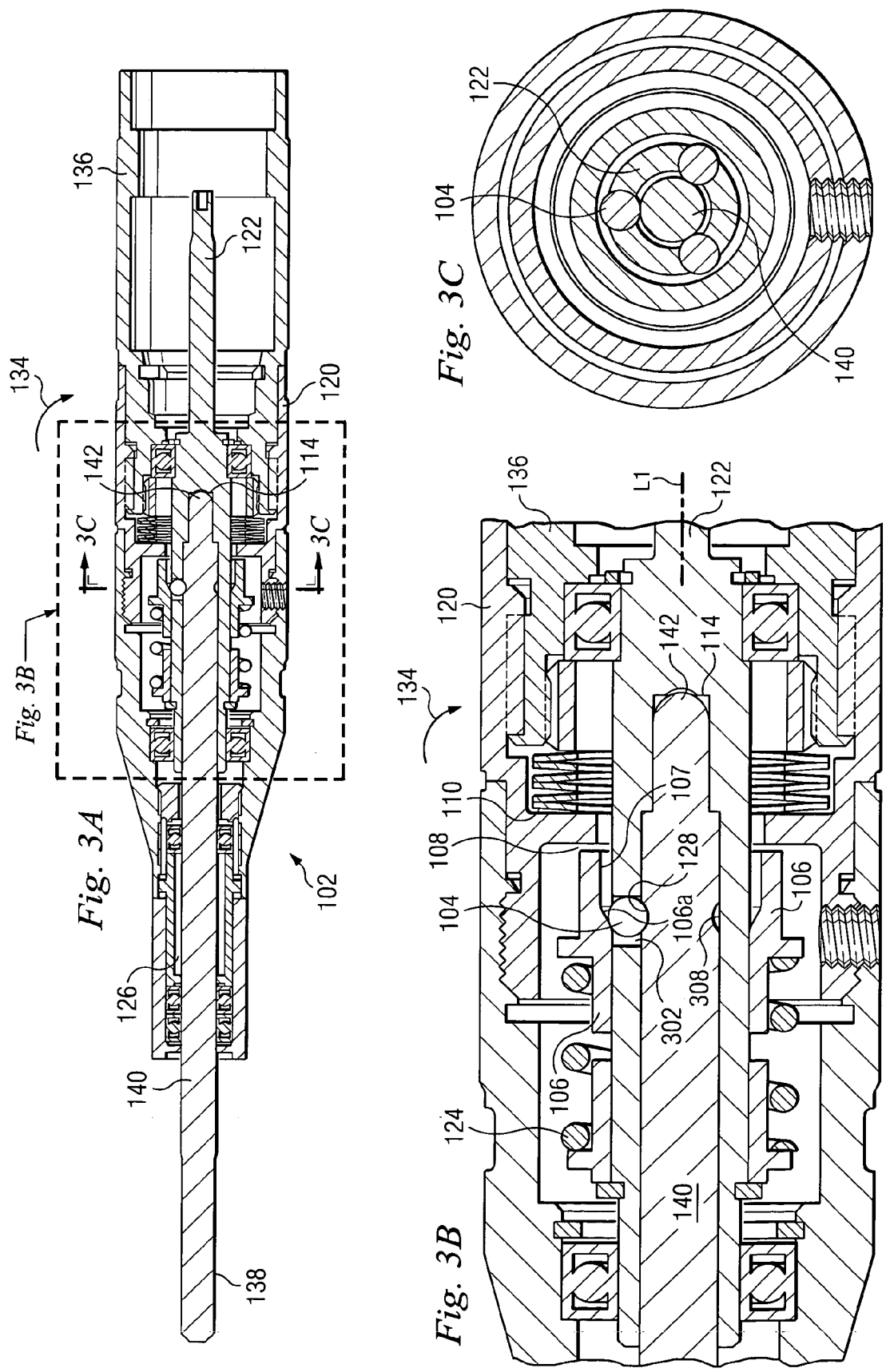

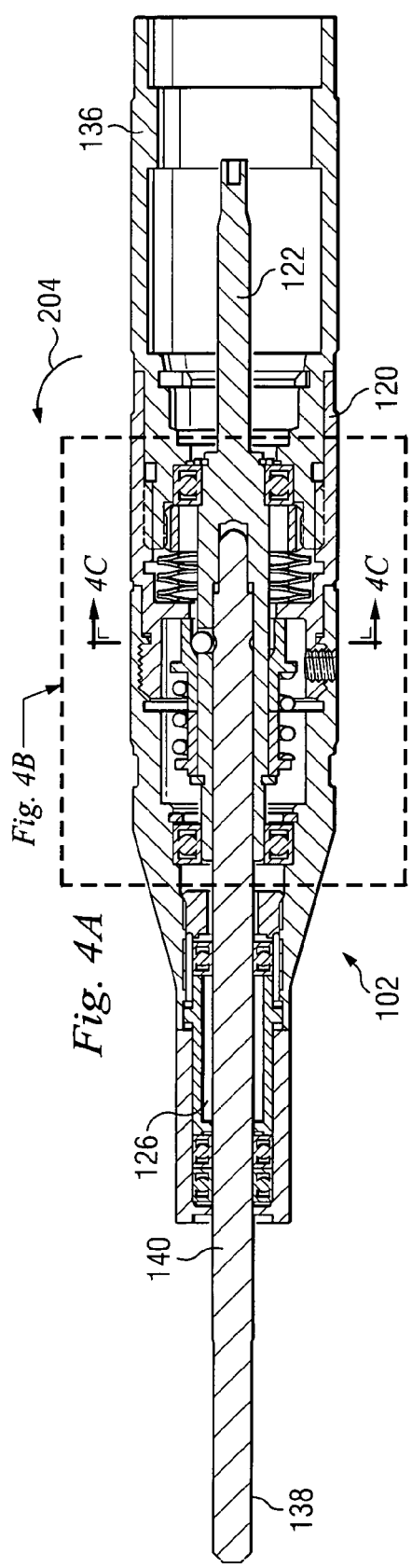
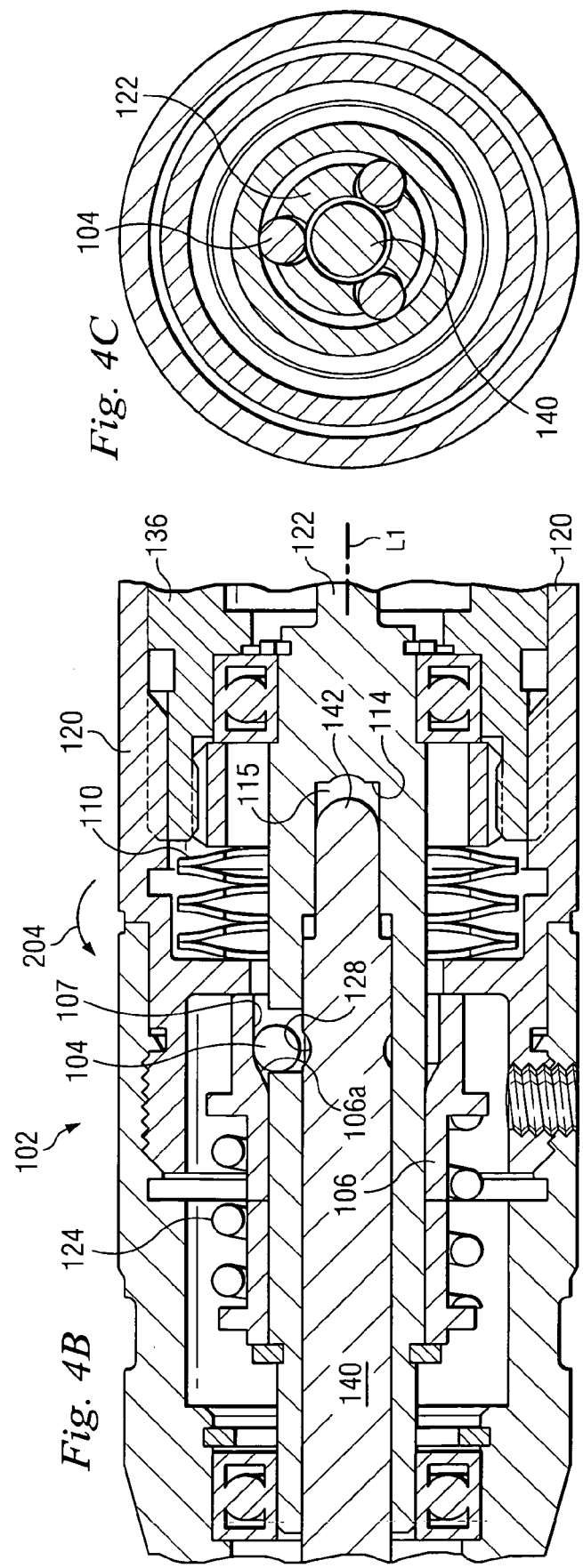

COUPLING SYSTEM FOR SURGICAL INSTRUMENT

FIELD OF THE INVENTION

The present invention relates generally to surgical instruments. More particularly, the present invention relates to coupling arrangements for surgical instruments.

BACKGROUND OF THE INVENTION

In various surgical procedures, it is necessary to dissect bone or other tissues. In some instances, it may be necessary to cut, grind, shape or otherwise remove hardened materials to make them ready for implantation or to remove them from a patient. Many conventional surgical instruments used for these purposes employ pneumatic or electrical motors to rotate a dissection element. In their most basic form, such a surgical instrument comprises a motor portion having a rotary shaft, a dissection tool having a cutting or abrading element that is rotated by the rotating shaft of the motor, and a coupling arrangement for connecting the dissection tool to a spindle or collet of the rotary shaft. The spindle or collet of the rotary shaft is usually housed within a base that is attached to the motor.

Since it is frequently necessary to replace the dissection tool, it is known in the art to use a quick release coupling to secure the dissection tool to the surgical instrument. An example of such a quick release coupling is shown and described in a commonly assigned U.S. Pat. No. 5,505,737, entitled "Quick Release Coupling For A Dissecting Tool," incorporated herein by reference in its entirety.

While currently known surgical tools, including replaceable dissection tools, offer advantages over earlier designs, it remains desirable to further advance the pertinent art of coupling arrangements for the dissection tools. For example, during a surgical procedure, a dissection tool may rotate at high speeds, for example approximately 70,000 rpm, and it may not be effectively retained with previously available coupling arrangements under all operating conditions.

SUMMARY OF THE INVENTION

In one embodiment, a coupling system for a medical dissection tool comprises: an internal passage adapted for receiving a portion of a medical dissection tool; and at least one locking member movable at least partially along the longitudinal axis through a first path into a locked position to prevent the medical dissection tool from moving along a longitudinal axis of the internal passage.

In another embodiment, a coupler for a powered medical tool comprises: an internal passage for receiving the powered medical tool; and a coupling assembly partially disposed within the internal passage and movable between a locked position and an unlocked position, wherein the coupling assembly comprises: a locking member; and an engagement sleeve for urging the locking member into the locked position through a first angled path.

Additional advantages and features of the present invention will become apparent from the following description and appended claims, taken in conjunction with the accompanying drawings.

Further areas of applicability of the present invention will become apparent from the detailed description provided hereinafter. It should be understood that the detailed description and specific examples, while indicating the embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2A illustrates a partially exploded perspective view of a surgical dissection tool according to one embodiment of the present invention.

FIG. 2B illustrates a partially assembled surgical dissection tool of FIG. 2A.

FIG. 2C illustrates an assembled surgical dissection tool of FIG. 2A.

FIG. 3A illustrates a partial cross-sectional side view of a medical dissection tool showing a locked coupling arrangement according to one embodiment of the present invention.

FIG. 3B illustrates an enlarged portion of the cross-sectional side view of the coupling arrangement of FIG. 3A.

FIG. 3C illustrates a transverse cross-sectional view of the coupling arrangement of FIG. 3A taken along line 3C-3C.

FIG. 4A is a partial cross-sectional side view of a medical dissection tool showing an unlocked coupling arrangement according to one embodiment of the present invention.

FIG. 4B is an enlarged portion of the cross-sectional side view of the coupling arrangement of FIG. 4A.

FIG. 4C is a transverse cross-sectional view of the coupling arrangement of FIG. 4A taken along line 4C-4C.

DETAILED DESCRIPTIONS

Figure 1:
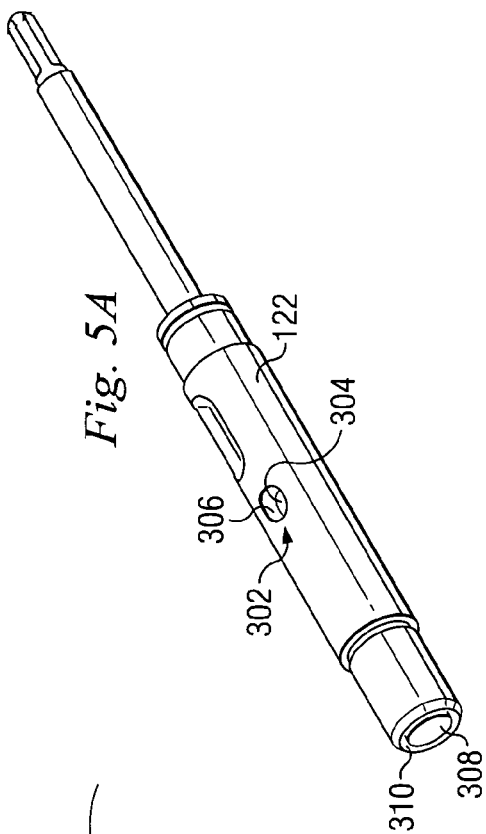
FIG. 1 illustrates a surgical dissection tool used in a human patient according to one embodiment of the present invention.

The present invention provides an improved coupling system and method of assembly for medical dissection instruments.

For the purposes of promoting an understanding of the principles of the invention, references will now be made to the embodiments, or examples, illustrated in the drawings, and specific languages will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring now to FIG. 1, in one embodiment, a human patient A is shown undergoing a neurological operation. As is a common practice, access to the brain or other neurological structures often requires delicate dissection of bone and other tissues B. By way of example, a dissection tool assembly 10 according to one embodiment of the present invention is shown being utilized to dissect a portion of patient A's bone and other tissues B adjacent to the surgical access site. It will be understood that the dissection tool assembly 10 will be described only briefly here, as various embodiments of dissection tool assemblies are disclosed in a U.S. Utility application Ser. No. 10/200,683 filed Jul. 22, 2002, which is hereby incorporated by reference in its entirety.

Referring now to FIGS. 2A through 2C, partial perspective views of one embodiment of the dissection tool assembly 10 are illustrated. The dissection tool assembly 10 includes a motor housing 12, which is coupled to an air supply and hose assembly 14 that supplies pressurized air to the motor and vents the low pressure exhaust air away from the surgical site. The dissection tool assembly 10 further includes an attachment housing 16 and a dissection tool 18. As shown in FIG. 2A, the distal portion 51 of the motor housing 12 includes a tapered leading portion 53 and a double D connection region. The double D connection region comprises a pair of opposing and substantially parallel planar portions interrupting the otherwise cylindrical body to define two opposing and substantially parallel cylindrical portions. These portions are separated by a junction 55 into a fixed segment having a cylindrical portion 54 and a flat portion 52, and a movable segment having a cylindrical portion 58 and a flat portion 56.

Referring now to FIG. 2B, the attachment housing 16 includes an internal cavity adapted to engage the distal portion 51 of the motor housing 12. Further, the attachment housing 16 and the distal portion 51 are configured to provide the user with a tactical feedback indicating a positive engagement. In an initial position with a first cylindrical portion 25 substantially abutting the motor housing 12, an attachment indicator mark 24 is in substantial alignment with an unlocked indicator mark 22 on the motor housing 12. In this position, the dissection tool 18 may be inserted into the attachment housing 16 and received in a coupling assembly (described later) within the motor housing 12.

Referring now to FIG. 2C, with the dissection tool 18 inserted within the attachment housing 16 and ready to be coupled with the motor housing 12 (see FIGS. 3A-3C), the attachment housing 16 may be rotated in the direction of arrow 23 with respect to the motor housing 12. Such rotation moves the attachment indicator marking 24 into a substantial alignment with a locked indicator mark 15 on the motor housing 12. As described further below, such rotation also locks the coupling assembly to prevent the dissection tool 18 from unintentional withdrawal from the attachment housing.

Coupling arrangements according to an illustrated preferred embodiment will now be described in detail, although the following description should not inhibit the application of the teachings of the invention to implementation in alternative forms. Specific reference will be made to the coupling assembly 102 shown illustrated in FIGS. 3A through 3C. Coupling assembly 102 includes a power shaft 122, adapted to be coupled to a motor 12, at least partially surrounded by an engagement sleeve 106. Movement of the engagement sleeve 106 with respect to the power shaft 122 is accomplished in a traditional manner through movement of the external portions of the device described with respect to FIGS. 2A through 2C.

Figure 5A:
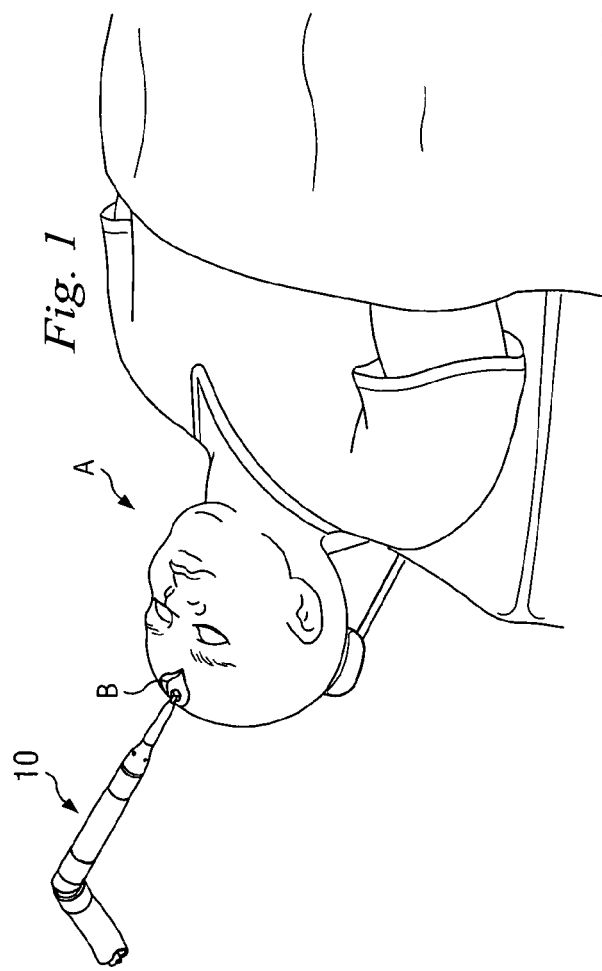
FIGS. 5A-5C illustrate details of a coupling shaft according to one embodiment of the present invention.
Figure 5B:
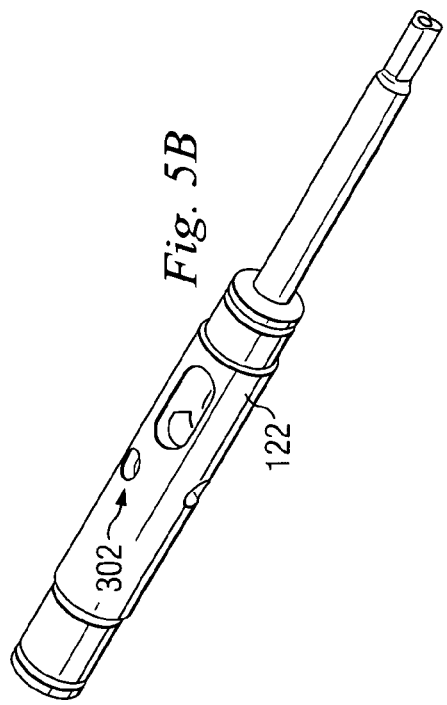
Figure 5C:
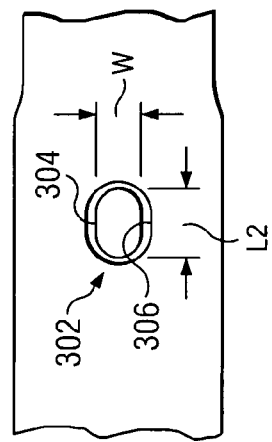

As shown more fully in FIGS. 5A through 5C, the power shaft 122 includes a longitudinal bore 308 having an open end 310 and an internal shoulder 114 (FIG. 3B). The channel or longitudinal bore 308 is configured to receive a proximal portion of the tool shaft 138 through the open end 310 and into abutting engagement with internal shoulder 114. An opening 302 extends between the outer surface of the power shaft 122 and the longitudinal bore 308. The opening 302 includes a lower portion 304 having a first perimeter and a top portion 306 having a second perimeter that is greater than the first perimeter. In a preferred aspect, the opening 302 transitions between the first perimeter and the second perimeter to form a substantially beveled edge. As described more fully below, a retention member 104 may extend into the opening 302 but contact with the beveled edge may prevent it from completely entering longitudinal bore 308. As shown in FIG. 5C, the opening 302 has a length L2 extending along the longitudinal axis L1 and a width W extending substantially transverse to the longitudinal axis. In a preferred aspect, L2 is greater than W such that the opening 302 takes the form of an elongated slot. Although an elongated slot extending along the longitudinal axis is shown for the purpose of illustration, it is contemplated that alternative configurations of the opening 302 may be utilized to implement the present invention without deviating from the teaching described herein.

Referring now to FIGS. 3A through 3C, the coupling assembly 102 is illustrated in a locked position. Retention member 104 is shown extending through the opening 302 in shaft 122 and into a retention groove 128 on tool shaft 140. The engagement sleeve 106 surrounds a portion of the power shaft 122 adjacent the openings 302. The engagement sleeve 106 includes an inner surface having a relief area 107 with a first internal diameter and an engagement surface 106a with a second minimum internal diameter less than the first diameter. The position of the engagement sleeve 106 with respect to the power shaft 122 is controlled by movement of the attachment housing 120 and the force of spring 124. In the locked position illustrated in FIGS. 3A through 3C, the engagement surface 106a is in contact with retention member 104. In the preferred embodiment illustrated, the engagement surface 106a is angled thereby imparting a first force on the retention member 104 inwardly transverse to the longitudinal axis and a second force along the longitudinal axis L1 toward internal shoulder 114. In this position, the force of spring 124, as applied through the engagement sleeve 106 and the retention member 104, urges the coupling end 142 of the tool shaft 140 against the internal shoulder 114.

FIGS. 4A through 4C, illustrate the coupling assembly 102 disposed in an unlocked position. In the unlocked position, the engagement sleeve 106 is positioned along the longitudinal axis such that the relief area 107 is axially positioned adjacent the retention member 104. In this position, the retention member 104 may exit the channel 308. Further, in this position the coupling end 142 of the tool shaft 140 may be spaced from the internal shoulder 114 creating a gap 115.

Referring now to FIGS. 3A and 3B, operation of the illustrated embodiments will be further described. In one embodiment, a medical dissection tool 138 is advanced within the longitudinal bore 308 until its coupling end 112 contacts a retention member 114, which is a part of a shaft 122. In one example, the coupling end 112 may comprise one or more planar surfaces adapted to mate with corresponding surfaces within bore 308 to impart rotational force to tool shaft 140.

Referring more specifically to the partially exploded perspective view of FIGS. 3B and 3C, as an attachment housing 120 is rotated in the direction of an arrow 134 with respect to a motor housing 136, it pushes a spring 110 along the longitudinal axis L1 and toward the motor housing 136, causing the spring 110 to become compressed. As a result, a gap 108 is created between the attachment housing 120 and engagement sleeve 106. At that point, spring 124 becomes relaxed, and its expansion pushes the engagement sleeve 106 in a direction parallel to the longitudinal axis L1 and toward the attachment housing 120. Since a contact surface 106a of the engagement sleeve 106 is sloped, it urges the locking member 106, which may be a spherical ball, through an angled path by moving both parallel to and toward the longitudinal axis L1. As a result, the locking member 104 will travel along the longitudinal axis L1 until it is adjacent groove 128 at which point the locking member will move inwardly into groove 128 Eventually, the locking member 104 will be pushed against a shaft 122. At that point, the engagement sleeve 106 and the shaft 122 will together secure the locking member 106 in the groove 128, thereby inhibiting movement of the shaft 140 along the longitudinal axis L1.

It is contemplated that the contact surface 106a may comprise a variety of shapes, such as a wedged shape, a partial spherical shape, as along as such a shape accommodates the movement of the locking member 104 through a angled path.

In this illustration, the locking member 104 is shown moving at an angled path, which is approximately 45° to the longitudinal axis L1, into the locked position. However, a variety of angles, which may range from approximately 0° through 90°, are also contemplated by the present invention.

In the illustrated embodiment, the groove 128 is concave-shaped from a longitudinal cross-sectional view, and does not actively participate in the transmission of any rotational force to the shaft 140. However, it is contemplated that the groove 128 may include surface configurations adapted to receive rotational force, and may thereby cooperate in driving the shaft 140.

Referring now to FIG. 3C, in one embodiment, to offer a triangle support, three locking members, each of which may be a spherical ball, maybe provided for the coupling assembly. It is contemplated that a fewer or greater number of locking members may also be utilized by the present invention. Further, the locking members may comprise other shapes, such as partially spheres or irregular shapes.

Referring now to FIGS. 4A-4C, in one embodiment, a coupling assembly 202 is shown in an unlocked position. Referring more specifically to the partially exploded perspective views of FIG. 4B and FIG. 4C, as the attachment housing 120 is rotated in the direction of an arrow 204 with respect to the motor housing 136, the force previously exerted on the spring 110 is released, causing the spring 110 to relax and move along the longitudinal axis L1 (toward the engagement sleeve 106). Meanwhile, as the attachment housing 120 is rotated, it advances toward the engagement sleeve 106 and closes the gap 108 of FIG. 3B. At that point, the engagement sleeve 106 is forced to move along the longitudinal axis L1 and toward the spring 124, causing the spring 124 to become compressed. As the engagement sleeve 106 moves further toward the spring 124, it no longer secures the locking member 104 in the groove 128. As a result, the locking member 104 moves out of the groove 128 by an angled trajectory-both parallel to the longitudinal axis L1 (and toward the direction of the spring 124) and away from the longitudinal axis L1.

Although only a few exemplary embodiments of this invention have been described above in details, those skilled in the art will readily appreciate that many modifications are possible in the exemplary embodiments without materially departing from the novel teachings and advantages of this invention. Also, features illustrated and discussed above with respect to some embodiments can be combined with features illustrated and discussed above with respect to other embodiments. Accordingly, all such modifications are intended to be included within the scope of this invention.

What is claimed is:

1. A coupling assembly for joining a power source to a medical dissection tool, the coupling assembly comprising:
   a coupling shaft having a proximal portion, an opposing distal portion, and a longitudinal axis extending therebetween, wherein the distal portion comprises an external surface and an internal surface, the internal surface defining a bore extending along the longitudinal axis for receiving a portion of the medical dissection tool,
   a first aperture extending from the external surface to the internal surface along a first axis substantially perpendicular to the longitudinal axis, the first aperture having a first length extending substantially along the longitudinal axis between a proximal wall and a distal wall, the first aperture having a first width extending substantially transverse to both the longitudinal axis and the first axis between a pair of sidewalls, wherein the first length is greater than the first width such that the first aperture is elongated along the longitudinal axis and wherein the proximal wall, distal wall, and pair of sidewalls extend in a direction substantially parallel to the first axis;
   a first locking member positioned at least partially within the first aperture and translatable along the longitudinal axis with respect to the coupling shaft from an unlocked positioned to a locked position to secure the medical dissection tool within the bore, wherein the first locking member is spaced from the proximal wall of the first aperture and adjacent to the distal wall of the first aperture in the unlocked position and wherein the first locking member is adjacent to the proximal wall of the first aperture and spaced from the distal wall of the first aperture in the locked position;
   an engagement sleeve disposed around the distal portion of the coupling shaft, the engagement sleeve having an internal contact surface for engagement with the first locking member, the internal contact surface extending at an oblique angle with respect to the longitudinal axis;
   a spring biasing the engagement sleeve towards the proximal portion of the coupling shaft; and
   an attachment housing disposed around the proximal portion of the coupling shaft for controlling the position of the engagement sleeve relative to the coupling shaft, the attachment housing moveable along the longitudinal axis relative to the coupling shaft by rotation of the attachment housing about the longitudinal axis;
   wherein the first locking member translates at an oblique angle relative to the longitudinal axis and the first axis when moved between the unlocked and locked positions.

2. The coupling assembly of claim 1, wherein the oblique angle is approximately 45°.

3. The coupling assembly of claim 1, wherein the first locking member comprises a spherical ball.

4. The coupling assembly of claim 1, further comprising a second aperture extending from the external surface to the internal surface along a second axis substantially perpendicular to the longitudinal axis, the second aperture having a second length extending substantially along the longitudinal axis and a second width extending substantially transverse to both the longitudinal axis and the second axis, wherein the second length is greater than the second width such that the second aperture is elongated along the longitudinal axis.

5. The coupling assembly of claim 4, further comprising a second locking member positioned at least partially within the second aperture and translatable along the longitudinal axis with respect to the coupling shaft from an unlocked positioned to a locked position to secure the medical dissection tool within the bore.

6. The coupling assembly of claim 5, wherein the second locking member translates at an oblique angle relative to the longitudinal axis and the second axis when moved between the unlocked and locked positions.

7. The coupling assembly of claim 5, wherein a portion of the internal contact surface of the engagement sleeve is configured for engagement with the second locking member.

8. The coupling assembly of claim 4, further comprising a third aperture extending from the external surface to the internal surface along a third axis substantially perpendicular to the longitudinal axis, the third aperture having a third length extending substantially along the longitudinal axis and a third width extending substantially transverse to both the longitudinal axis and the second axis, wherein the third length is greater than the third width such that the second aperture is elongated along the longitudinal axis.

9. The coupling assembly of claim 8, further comprising a third locking member positioned at least partially within the third aperture and translatable along the longitudinal axis with respect to the coupling shaft from an unlocked positioned to a locked position to secure the medical dissection tool within the bore.

10. The coupling assembly of claim 1, wherein the second and third locking members each comprise a spherical ball.

* * * * *